United States Patent [19]

Kyle

[11] Patent Number: 5,374,657
[45] Date of Patent: Dec. 20, 1994

[54] MICROBIAL OIL MIXTURES AND USES THEREOF

[75] Inventor: David J. Kyle, Catonsville, Md.

[73] Assignee: Martek Corporation, Columbia, Md.

[21] Appl. No.: 944,739

[22] Filed: Sep. 14, 1992

Related U.S. Application Data

[63] Continuation of Ser. No. 645,457, Jan. 24, 1991, abandoned.

[51] Int. Cl.⁵ .................. A61K 31/225; A61K 31/20
[52] U.S. Cl. .................................. 514/547; 514/560
[58] Field of Search ............................. 514/560, 547

[56] References Cited

U.S. PATENT DOCUMENTS

| | | | |
|---|---|---|---|
| 2,611,706 | 9/1952 | Bernhart et al. | 99/118 |
| 2,923,628 | 2/1960 | Otto | 99/63 |
| 3,458,625 | 7/1969 | Ensor et al. | 424/95 |
| 3,542,560 | 11/1970 | Tomarelli et al. | 99/63 |
| 3,649,295 | 3/1972 | Bernhart | 99/57 |
| 4,058,594 | 11/1977 | Williams | 424/37 |
| 4,216,236 | 8/1980 | Mueller et al. | 426/72 |
| 4,282,265 | 8/1981 | Theuer | 426/607 |
| 4,303,692 | 12/1981 | Gaull | 426/580 |
| 4,513,008 | 4/1985 | Revici et al. | 514/560 |
| 4,526,793 | 7/1985 | Ingenbleek et al. | 426/72 |
| 4,526,902 | 7/1985 | Rubin | 514/560 |
| 4,544,559 | 10/1985 | Gil et al. | 426/72 |
| 4,614,663 | 9/1986 | Rule | 426/601 |
| 4,670,285 | 6/1987 | Clandinin et al. | 426/602 |
| 4,752,618 | 6/1988 | Mascioli et al. | 514/549 |
| 4,780,456 | 10/1988 | Pistolesi et al. | 514/78 |
| 4,820,731 | 4/1989 | Mascioli et al. | 514/549 |
| 4,826,877 | 5/1989 | Stewart et al. | 514/560 |
| 4,843,095 | 6/1989 | Rubin | 514/558 |
| 4,874,603 | 10/1989 | Fratzer | 424/10 |
| 4,876,107 | 10/1989 | King et al. | 426/601 |
| 4,920,098 | 4/1990 | Cotter et al. | 514/2 |
| 4,938,984 | 7/1990 | Traitler et al. | 426/580 |
| 5,130,242 | 7/1992 | Barclay | 435/134 |

FOREIGN PATENT DOCUMENTS

| | | |
|---|---|---|
| 269351 | 6/1988 | European Pat. Off. |
| 3603000 | 8/1987 | Germany |
| 80250 | 3/1989 | Japan |
| 1132371 | 5/1989 | Japan |
| 196255 | 8/1989 | Japan |
| 215245 | 8/1989 | Japan |
| 8900606 | 1/1989 | WIPO |
| 9013656 | 11/1990 | WIPO |

OTHER PUBLICATIONS

Shinmen, et al. ,*Appl. Microbiol. Biotechnol.*, 31:11–16 (1989).
Bjerve, et al., *Am. J. Clin. Nutri.*, 57 (Suppl.):801S–6S (1993).
Carlson, et al., *Essential Fatty Acids and Eicosenoids*, p. 192, A. Sinclair and R. Gibson, eds. (1992).
Less and Karel, eds., *Omega-3 Fatty Acids in Health Disease*, (1990), p. 136.
Kyle, *Advances Applied Biotech.*, 12:168–193 (1991).
Weaver, et al., in *Health Effects of Fish and Fish Oils*, (Clandra, Ed.) pp. 581–590 (1989).
Ackman, *Fats for the Future: Problems in Fish Oils and Concentrates*, (Cambie, Ed.) pp. 189–200 (1989).
Puppione et al., in *Dietary ω-3 and ω-6 Fatty Acids*, (Galli et al., Ed.) pp. 361–365 (1988).
Kolestzko, Abstract from 3d Int. Congress on Polyunsaturated Fatty Acids in Adelaide, Australia (1992).
Sanders et al., *American Journal of Clinical Nutrition*, 31:805–813 (1978).
Carlson et al., *Inform*, 1:306 (1990).
Burre et al., *Lipids*, 25:354–356 (1990).
International Search Report to WO/90/13656 (1990).
CA 100:66638d, Kane, 1983.
CA 104:4865z, Ito et al., 1985.
CA 107:57830c, Carlson et al., 1987.
CA 113:39304d, Yeh et al., 1990.

Primary Examiner—Marianne M. Cintins
Assistant Examiner—Kimberly R. Jordan
Attorney, Agent, or Firm—Banner, Birch, McKie & Beckett

[57] ABSTRACT

The present invention relates to compositions including blends of microbial oils, methods of using such compositions, particularly as supplements for infant formula, and methods of increasing the amount of long chain polyunsaturated fatty acids in infant formula.

22 Claims, No Drawings

MICROBIAL OIL MIXTURES AND USES THEREOF

This is a continuation of application Ser. No. 07/645,457, filed Jan. 24,1991, now abandoned.

This invention relates to blends or mixtures of polyunsaturated fatty acid-containing microbial oils and to uses thereof. In a specific preferred embodiment, this invention concerns the use of such oils as an additive or supplement for human diets, for example, as an additive to infant formula.

It long has been known that long chain polyunsaturated fatty acids (PUFAs) are essential to the human diet, particularly during periods of rapid tissue growth. Sanders et al, *Am. J. Clin. Nutr,* 31:805–813 (1978). Certain of these long chain acids, such as arachidonic acid (ARA), cannot be synthesized de novo in humans. Only by metabolizing linoleic acid (LOA), which is connected to gamma linolenic acid (GLA), and then to ARA can the human body produce ARA. LOA, in turn, is an essential acid which can only be obtained from dietary sources. Additionally, the presence of eicosapentaenoic acid (EPA) in the diet inhibits the metabolic conversion of LOA to ARA. Carlson, et al., *INFORM,* 1:306 (1990). ARA and docosahexaneoic acid (DHA) are critical elements of muscle, organ and vascular tissues.

Infancy is the most significant period of rapid growth in a human's life. An infant can increase its body weight by three times or more during its first year of life. Accordingly, it is critical that the infant receive adequate amounts of PUFAs to insure proper structural and organ development. Human breast milk contains high levels of PUFAs in which the ratio of ARA to EPA is typically about 20:1. However, many women choose not to breast feed their infants for either part or all of the first year of the infant's life.

As recognized by Clandinin et al., U.S. Pat. No. 4,670,285, incorporated herein by reference, available infant formulas are deficient in long chain ($C_{20}$ and $C_{22}$) PUFAs. Clandinin et al. disclose an infant formula prepared from a blend of vegetable oil and egg yolk lipid and/or fish oil which can provide a total fat composition comparable to that of human breast milk. A preferable composition comprises from 75 to 95 parts weight egg yolk and 5 to 25 parts vegetable oil. This composition is the entire lipid content of the infant formula and it is not economical to prepare. Additionally, the infant formula disclosed by Clandinin et al. results in an EPA level which is 16 times higher than the level of EPA in human breast milk and fan ARA level which is only one quarter that of breast milk.

DE 3603000A1 (Milupa) discloses a computer profile of a highly polyunsaturated acid fat mixture and discusses the use of such a mixture to produce infant formulas. Sources of the fatty acids are listed as certain types of macroalgae (i.e. seaweed), fish oil, organ fats from beef and pork, and highly refined egg yolk oil. In addition to DHA from fish oil, a potential source of DHA and ARA is said to be macroalgae, but only of the seaweed types. There is no suggestion to use microbes of any type, much less microbial oil.

Methods of producing microbial oils are disclosed in the following references, each of which is incorporated herein by reference. Co-pending U.S. patent application Ser. No. 07/496,572, filed Mar. 21, 1990, now U.S. Pat. No. 5,244,921 discloses the production of eicosapentaneoic acid-containing single cell oils (EPASCO). Co-pending U.S. patent application Ser. No. 07/479,135, filed Feb. 13, 1990, discloses the production of docosahexaneoic acid-containing single cell oil (DHASCO). Co-pending U.S. patent application Ser. No. 07/645,454, now abandoned filed concurrently with the present application and assigned to the same assignee, relates to the production of arachidonic acid-containing single cell oil (ARASCO). EP322,227 also discloses a microbial oil production system. None of these references teach the use of blends containing unmodified microbial oils as a dietary supplement, or the use of a blend of microbial oils as an additive to existing infant formula to provide that formula with a long chain PUFA composition similar to breast milk.

Accordingly, it is an object of the present invention to provide a PUFA-enriched additive, the composition of which when added to commercial infant formula will provide desired long chain PUFAs in amounts comparable to the amounts of those PUFAs found in human breast milk.

It is an additional object of the present invention to provide an economical method of producing the above-described composition.

These, and other, objects are satisfied by the present invention as described herein.

SUMMARY OF THE INVENTION

This invention relates to the use of microbial oils which contain long chain polyunsaturated fatty acids. Additionally, in various embodiments, fish oil and/or vegetable oils can be blended with such microbial oils to form desired compositions. The compositions can be used as dietary supplements, particularly as additives for infant formula, as well as for pharmaceutical and cosmetic applications.

The invention also relates to economically viable processes for altering the long chain polyunsaturated fatty acid composition of infant formula and/or baby food. Preferably, the altered composition resembles that of human breast milk.

DETAILED DESCRIPTION OF THE PREFERRED EMBODIMENT OF THE INVENTION

Broadly stated, the present invention concerns blends, or mixtures, containing unmodified microbial oils. As used herein, "unmodified" means not chemically or covalently altered. It will be understood that throughout this specification references to "microbial oil" or "oil" mean, unless otherwise specifically stated, unmodified oil. "Microbial oils" or "single cell oils" are those oils naturally produced by microorganisms during their lifespan. Such oils can be high in long chain PUFAs. The applicant has discovered that certain of these oils, when blended with other microbial oils, fish oils, vegetable oils, or any combination thereof, can produce a composition useful for dietary, pharmaceutical or cosmetic purposes.

Various microbial oils, for example, can be obtained by, for example, the processes disclosed in above-referenced U.S. patent applications Ser. No. 07/496,572, now U.S. Pat. No. 5,244,921, 07/479,135, EP322,227 (Yamada et al., Suntory) or U.S. patent application Ser. No. 07/645,454, now abandoned, (the latter having been filed concurrently with the present application and assigned to the same assignee). The disclosure of each of these references is specifically incorporated by reference herein. As used herein, "single cell oil" refers to a triglyceride product of a unicellular organism.

It is to be understood that the present invention encompasses the use of a single-microbial oil containing at least two desirable PUFAs, such as ARA and DHA. The oils specifically disclosed and utilized herein, however, each contain a single desirable PUFA.

Any non-toxic, PUFA-containing microbial oil can be used in the present invention. The most preferred microbial oils are those rich in an omega-3 or omega-6 PUFA, especially DHA, GLA or ARA. These PUFAs typically are missing from, or are inadequately provided in, dietary supplements such as infant formulas or baby food. "Infant formula" as used herein means an enteral nutritional product which can be substituted for human breast milk in feeding infants and typically is composed of a desired percentage of fat mixed with desired percentages of carbohydrates and proteins in an aqueous solution. Frequently micronutrients, such as trace metals and vitamins or other desired additives are present. An exemplary formula is disclosed by Clandinin et al., U.S. Pat. No. 4,670,285, the disclosure of which is incorporated herein by reference.

In the present invention, types of oils from different microbes can be mixed together to obtain a desired composition. Alternatively, or additionally, PUFA-containing microbial oil can be blended with fish oil, vegetable oil or a mixture of both to obtain a desired composition.

An objective in mixing the oils is to obtain an additive which will provide an infant formula with a desired omega-3 and omega-6 PUFA composition similar to that found in breast milk. While the proportion of the desired fatty acids in a microbial oil can vary, this proportion can easily be determined and the amount of oil adjusted to provide the desired amount of PUFA. Similarly, the percentage of desired PUFA in fish oil or vegetable oils can easily be determined and the amount of the oil to be added can be adjusted as necessary to achieve the desired results.

"Fish oils" are those oils obtained from fish. Such oils typically contain DHA in amounts ranging from 3% to about 20%. Typically, however, fish oils also contain EPA which depresses the production of ARA in the body. The addition of a microbial oil containing high levels of ARA to fish oil-containing compositions substantially overcomes that problem.

"Vegetable oil" includes all those oils from plants which contain PUFAs. Typically, vegetable oils do not contain long chain PUFAs (PUFAs at least 20 carbons long), which is why animal organ oils are usually characterized as the source of PUFAs. Thus, vegetarians, especially vegetarian mothers, can have a diet containing inadequate amounts of PUFAs. Vegetable oils known to contain PUFAs may contain GLA. GLA is a C18:3 omega-6 PUFA. Such oils include black currant seed oil, borage oil and primrose oil. While GLA is the metabolic precursor to ARA, the process of conversion is very slow, requiring the participation of the enzyme Δ6-desaturase. This enzyme is present in humans in very low levels. Burre, et al., *Lipids*, 25:354–356 (1990). Thus, it would be preferable to provide the body with ARA rather than its precursor, GLA.

Methods for isolating vegetable oils are known to those of skill in the art and do not comprise a part of the present invention. Additionally, certain fungi produce PUFA-containing oils. For example, Mucor species produce a GLA-containing oil.

DHASCO, defined herein as docosahexaneoic acid-containing single cell oil, can be obtained, for example, from *Crypthecodinium cohnii* as disclosed above-referenced U.S. application Ser. No. 07/479,135. DHA is a C22:6 omega-3 long chain PUFA.

Microorganisms capable of producing a single cell oil containing DHA are cultivated in a fermentor in a nutrient solution capable of supporting the growth of such organisms. Preferably the single cell oil will contain at least about 20% by weight DHA.

Any microorganisms capable of producing a single-cell edible oil containing DHA can be used in the present invention. For example, photosynthetic diatoms can be used. Preferred microorganisms are marine dinoflagellates, including Crypthecodinium sp. Especially preferred is *Crypthecodinium cohnii*, an obligate heterotroph requiring a reduced carbon source for growth. *C. cohnii* is preferred because it contains a fatty acid profile in which DHA is the only PUFA present in sufficient quantities (greater than about 1% of the total amount of PUFAs). Samples of this organism, designated MK8840, have been deposited with the American Type Culture Collection at Rockville, Md., and assigned accession number 40750. As used herein, microorganism, or any specific type of microorganism, includes wild strains, mutants or recombinant types. Any microorganism which produces enhanced levels of oil containing DHA is considered to be within the scope of this invention. One of the features of the present invention is its recognition of the edible oil-producing capability of microorganisms such as dinoflagellates and the attendant solution to the problem of maintaining a reliable, economic source of such oils. Accordingly, wild-type and recombinant microorganisms designed to produce single cell oil containing DHA are an aspect of this invention. Such recombinant organisms would include those designed to produce greater quantities of DHA in the single cell oil, greater quantities of total oil, or both, as compared to the quantities produced by the same wild type microorganism, when provided with the same substrates. Also included would be microorganisms designed to efficiently use more cost-effective substrates while producing the same amount of single cell oil containing DHA as the comparable wild-type microorganism.

In general, those of skill in the art would not consider *C. cohnii* a suitable organism for cultivation in a fermentor. Previous workers have commented on the extremely complex mixture of nutrients required to successfully cultivate *C. cohnii*. Gold et al. *Protozoal*, 13:255–257 (1966); Guillard, et al. in "Dinoflagellates", Academic Press (1984); Henderson, et al., *Phytochemistry* 27:1679–1683 (1988). In contrast, the present invention achieves the cultivation of DHA-producing microorganisms in a simple medium containing glucose and yeast extract. Use of these components in a solution such as seawater provides economically significant growth rates and cell densities. For example, during the course of a 3–5 day fermentation, *C. cohnii* cell densities of at least 10 grams of biomass per liter of solution, and typically from 20 to about 40 grams per liter, can be attained. Such densities have not heretofore been attainable.

Although cultivation can occur in any suitable fermentor, preferably the organism is grown either in a stirred tank fermentor (STF) or in an air lift fermentor (ALF), both types known to those of skill in the art. When a STF is selected, agitation is provided using either Rushton-type high efficiency turbines or pitched-blade or marine impellers. Agitation and duration renews the supply of oxygen to the microorganisms. The rate of agitation normally is increased as the biomass increases, due to the increased demand for oxygen. It is desirable to keep the tip speed at not greater than about 500 cm/sec. Selection of strains of microorganisms which are capable of withstanding greater tip speeds without undergoing shear is within the purview of those of skill in the art. The use of such strains is expressly included in this invention.

As noted above, seawater is an acceptable medium for the nutrient solution. The seawater can be either natural, filtered or an artificial mix, each of which can be diluted to $\frac{1}{2}$ strength with tap water or concentrated to 2 times normal strength. A preferred example is Instant Ocean ® (IO) brand artificial seawater. Although C. cohnii is a marine microorganism, some growth has been observed in zero salinity. The use of variants which grow well in reduced salinities is specifically encompassed by this invention. Micronutrients can be added and may be required. However, such micronutrients are known to those of skill in the art and generally are present in seawater or tap water. If the organism selected is heterotrophic, such as C. cohnii, then a carbon source is added.

Preferably, after addition of the seawater medium to the fermentor, the fermentor containing the medium is sterilized and cooled prior to adding the nutrients and a seeding population of microorganism. (Although it is acceptable to sterilize the nutrients together with the seawater, sterilization in this manner can result in a loss of available glucose.) The nutrients and microorganism can be added simultaneously or sequentially.

An effective seed concentration can be determined by those of skill in the art. When a STF is used, the addition of a population of from about 0.05 to 1.0 grams of dry weight equivalent per liter at the beginning of the fermentation is preferred. This is about $10^5$ cells per ml. Thus, for a 30 liter fermentor, 1.5 liters of seeding media, containing viable cells at a density of 20 g dry weight per liter would be added.

Oxygen levels preferably are maintained at a D.O. of at least about 10% of air saturation level. Biosynthesis of DHA requires oxygen and, accordingly, higher yields of DHA require D.O. levels at from about 10% to 50% of air saturation levels. Agitation tip speeds of 150-200 cm/sec in combination with an aeration rate of 1 VVM (volume of air/volume of fermentor per minute) provides D.O. levels of from about 20% to about 30% at biomass densities of about 25 g dry weight/liter of culture. Higher cell densities may require higher D.O. levels, which can be attained by increased aeration rates by O2 sparging, or by increasing the air pressure in the fermentor.

Acceptable carbon sources are known to those of skill in the art. For example, carbon can be provided to C. cohnii in the form of glucose. Other heterotrophs can use other reduced carbon sources, a matter easily determined by those of skill in the art, and autotrophs utilize carbon dioxide. C. cohnii will also grow on other reduced, more complex, carbon sources. Typically, a fermentation is initiated with about 10-20 g/liter glucose. More glucose is added during the fermentation as required. Alternatively, from about 80 to 150 g glucose/liter initially can be added, thereby minimizing the frequency of future additions. If glucose levels drop to zero, the culture can die within a few hours. The amount of carbon source provided to other organisms can readily be determined by those of skill in the art.

In addition to a reduced carbon source, a nitrogen source, such as yeast extract (YE), is provided to the medium. Commercially available yeast extract is acceptable. For example, DIFCO brand yeast extract can be used. The yeast extract is an organic nitrogen source also containing micronutrients. Other organic nitrogen sources can easily be determined by those of skill in the art. However, such compounds are more expensive than yeast extract. The use of variants capable of growing on urea or nitrates is within the scope of this invention. Typically, the fermentation is initiated with about 4-8 g YE/liter. More YE can be added as required. A typical fermentation run requires about 25 to 50 g YE/liter over the course of the run. Accordingly, that amount of YE can be added initially with a reduced need for further additions. The precise amount can be determined by those of skill in the art.

The cultivation can be carded out at any life-sustaining temperature. Generally C. cohnii will grow at temperatures ranging from about 15° C. to 34° C. Preferably the temperature is maintained at about 20-28° C. Strains which grow at higher temperatures are preferred, because they will have a faster doubling time, thereby reducing the fermentation time. Appropriate temperature ranges for other microorganisms are readily determined by those of skill in the art.

The cultivation can be carried out over a broad pH range, typically from about pH 5.0 to 9.0. Preferably, a pH range of from about 7.0 to about 7.8 is used. The initial growth tends to acidify the medium. Addition of a base, such as KOH or NaOH, corrects this acidification. During the later stages of the fermentation, the culture medium tends to become alkaline. The addition of YE ordinarily is sufficient to maintain the pH in the desired range. However, if desired, inorganic acid pH controls can be used to correct alkalinity.

Production of the single cell oil is induced in the dinoflagellates by the imposition of a nitrogen deficiency. Such deficiencies are caused by providing YE in a limiting amount such that the medium runs out of YE while available glucose remains. The present invention recognizes that it is the carbon source to nitrogen source ratio which promotes the efficient production of the single cell oil. Using glucose and YE as exemplary, a preferred ratio of carbon source to nitrogen source is about 2-4 parts glucose to 1 part YE. Similar ratios for other carbon and nitrogen sources can be calculated by those of skill in the art.

After induction of oil production, the culture is grown for about 24 additional hours. During this period of oleosynthesis, the single cell oil containing DHA is being synthesized and visible oil droplets become apparent. Those of skill in the art can readily calculate the time of fermentation required to achieve the expected amount of cell biomass based upon the added amount of YE. When that time has passed, the culture is grown for an additional 24 hours and harvested. In general the C. cohnii are cultivated for a time sufficient to produce single cell oil, usually from about 60 to about 90 hours, although this time is subject to variation.

From about 20 to 30% of the resultant biomass, using wild-type C. cohnii, comprises extractable oil. Strain selection can increase this percentage and such selection is within the scope of this invention. Preferably, the oil comprises greater than about 90% triglycerides having, in general, the following fatty acid composition.

15–20% myristic acid ($C_{14:0}$)
20–25% palmitic acid ($C_{16:0}$)
10–15% oleic acid ($C_{18:1}$)
40–45% DHA ($C_{22:6}$)
0–5% others The crude oil is characterized by a yellow-orange color and is liquid at room temperature. Desirably, the oil contains at least about 20% DHA by weight and most preferably at least about 35% DHA by weight.

The organisms are harvested by conventional means, known to those of skill in the art, such as centrifugation, flocculation or filtration, and can be processed immediately or dried for future processing. In either event, the oil can be extracted readily with an effective amount of solvent. Suitable solvents can be determined by those of skill in the art. However, a preferred solvent is pure hexane. A suitable ratio of hexane to dry biomass is about 4 liters of hexane per kilogram of dry biomass. The hexane preferably is mixed with the biomass in a stirred reaction vessel at a temperature of about 50° C. for about 2 hours. After mixing, the biomass is filtered and separated from the hexane containing the oil. The residual biomass, i.e. The single cell edible oil extracted biomass of the microorganisms, such as *C. cohnii*, can be used as an animal feed, containing as it does about 35–40% protein, 8–10% ash and 45–50% carbohydrates. The hexane then is removed from the oil by distillation techniques known to those of skill in the art. Conventional oilseed processing equipment is suitable to perform the filtering, separation and distillation. Additional processing steps, known to those of skill in the art, can be performed if required or desirable for a particular application. These steps also will be similar to those involved in conventional vegetable oil processing and do not comprise a part of this invention.

EPASCO, defined herein as eicosapentaneoic acid-containing single cell oil, can be obtained, for example, from Nitzschia alba as disclosed in above-referenced U.S. application Ser. No. 07/496,572, now U.S. Pat. No. 5,244,921. EPA is a C20:5 omega-3 long chain PUFA.

ARASCO, defined herein as arachidonic acid-containing single cell oil, can be obtained from species such as *Pythium insidiosum*, or *Mortierella alpina*, as described in U.S. application Ser. No. 07/645,454, now abandoned filed concurrently herewith. ARA is a C20:4 omega-6 long chain PUFA.

Of those fungal species which previously have had their fatty acids characterized, it has been found that most do not make ARA. Weete, J. D., *Fungal Lipid Biochemistry*, Plenum Press, N.Y. (1974). Of those species which do make ARA, many, including all previously characterized Pythium species, produce significant quantities of eicosapentaenoic acid (EPA) in addition to ARA. Unexpectedly, it has been found that *P. insidiosum* produces ARA without concomitant production of EPA. As with fish oils, high EPA levels in dietary supplements result in a depression of the ability to form ARA from dietary linoleic acid (LOA). Accordingly, while those fungal species producing both ARA and EPA can be utilized in the process of this invention, it is preferable to use species which do not produce significant quantities of EPA. Such preferred species include *Pythium insidiosum* and *Mortierella alpina*. Both species are available commercially and are on deposit with the American Type Culture Collection in Rockville, Md., having accession numbers 28251 and 42430, respectively. Throughout this disclosure, unless otherwise expressly stated, *P. insidiosum* will be the representative fungal species.

One of the significant problems which an embodiment of the present invention overcomes, is the depression of ARA biosynthesis in infants caused by the presence of enhanced dietary levels of EPA. This problem can be corrected by providing ARA for use in infant formula at levels substantially similar to those found in human breast milk. Typically in human breast milk, the ratio of ARA:EPA is about 20:1 respectively. The present invention specifically contemplates any microbial oil which provides a sufficient amount of ARA to overcome the negative effects of dietary EPA. Preferably, the use of the ARA-containing oil will result in an ARA:EPA ratio of at least about 5:1. More preferably, the ratio will be at least about 10:1 and, most preferably, it will be at least about 20:1. As can be seen, the higher the amount of ARA in the end product, with respect to the amount of EPA, the more desirable is the result.

In a process of the present invention, the fungi are cultivated under suitable ARA-containing oil producing cultivating conditions. In general, techniques of fungal cultivation are well known to those of skill in the art and those techniques can be applied to the present inventive process. For example, cultivation of an inoculating amount of fungus can occur in submerged culture in shake flasks. The flask is provided with a growth medium, seeded with fungal mycelium, and grown on a reciprocating shaker for about three to four days.

The composition of the growth medium can vary but always contains carbon and nitrogen sources. A preferred carbon source is glucose, amounts of which can range from about 10–100 grams glucose per liter of growth medium. Typically about 15 grams/liter are utilized for shaker flask culture. The amount can be varied depending upon the desired density of the final culture. Other carbon sources which can be used include molasses, high fructose corn syrup, hydrolyzed starch or any other low cost conventional carbon source used in fermentation processes. Additionally, lactose can be provided as a carbon source for *P. insidiosum*. Thus, whey permeate, which is high in lactose and is a very low cost carbon source, can be used as a substrate. Suitable amounts of these carbon sources can readily be determined by those of skill in the art. Usually, additional carbon needs to be added during the course of the cultivation. This is because the organisms use so much carbon that adding it all in a batch mode could prove unwieldy.

Nitrogen typically is provided in the form of yeast extract at a concentration of from about 2 to about 15 grams extract per liter of growth medium. Preferably, about four grams per liter are provided. Other nitrogen sources can be used, including peptone, tryptone, corn-steep liquor, etc. The amount to be added of these sources can easily be determined by those of skill in the art. Nitrogen can be added in a batch mode, i.e. all at one time prior to cultivation.

After cultivation for 3–4 days at a suitable temperature, typically about 25°–30° C., in amount of fungi has grown which is sufficient for use as an inoculum in a conventional stirred tank fermentor (STF). Such fermentors are known to those of skill in the art and are commercially available. Fermentation can be carried out in batch, fed-batch, or continuous fermentation modes. Preferably, the STF is equipped with a Rushton-type turbine impeller.

The fermentor is prepared by adding the desired carbon and nitrogen sources. For example, a 1.5 liter fermentor can be prepared by mixing about 50 grams of glucose and about 15 grams of yeast extract per liter of tap water. As previously discussed, other carbon or nitrogen sources or mixtures thereof can be used.

The reactor containing the nutrient solution should be sterilized by, for example, heating prior to inoculation. After cooling to about 30° C., the inoculum can be added, and cultivation initiated. Gas exchange is provided by air sparging. The air sparging rate can vary, but preferably is adjusted to from about 0.5 to about 4.0 VVM (volume of air per volume of fermentor per minute). Preferably the dissolved oxygen level is kept at from about 10% to about 50% of the air saturation value of the solution. Accordingly, adjustments in the sparge rate may be required during cultivation. Agitation is desirable. The agitation is provided by the impeller. Agitation tip speed preferably is set within the range of from about 50 cm/sec to about 500 cm/sec, preferably from about 100 to 200 cm/sec.

In general, the amount of inoculum can vary. Typically, from about 2% to about 10% by volume of inoculum can be used. Preferably, in a fermentor seed train about 5 % by volume of inoculum can be used.

Nutrient levels should be monitored. When glucose levels drop below 5 g/l, additional glucose should be added. A typical cultivation cycle utilizes about 100 grams of glucose and about 15 grams of yeast extract per liter. It is desirable to deplete the nitrogen during the coarse of the cultivation as this enhances oil production by the fungi. This is especially true when *M. alpina* is used as the production organism.

Occasionally, the culture will produce an excessive quantity of foam. Optionally, an antifoaming agent, such as those known to those of skill in the art, e.g. Mazu 310®, can be added to prevent foam.

The temperature of cultivation can vary. However, those fungi which produce both ARA and EPA tend to produce less EPA and more ARA when cultivated at higher temperatures. For example, when *Mortierella alpina* is cultivated at less than 18° C., it begins to produce EPA. Thus, it is preferable to maintain the temperature at a level which induces the preferential production of ARA. Suitable temperatures are typically from about 25° C. to about 30° C.

Preferably, cultivation continues until a desired biomass density is achieved. A desirable biomass is about 25 g/l of the organism. Such a biomass typically is attained within 48–72 hours after inoculation. At this time, the organisms typically contain about 5–40 % complex lipids, i.e. oil, of which about 10–40% is ARA, and can be harvested.

Harvesting can be done by any suitable method such as, for example, filtration, centrifugation, or spray drying. Because of lower cost, filtration may be preferred.

After harvesting, the mycelial cake can be extracted. The mycelial cake refers to the collection of biomass resulting after harvest. The cake can be loose or pressed, crumbled or uncrumbled. Optionally, the cake can have any residual water removed, as by vacuum drying or lyophilization, prior to extraction. If this option is selected, it is preferable to use nonpolar solvents to extract the ARA-containing oil. While any non-polar extract is suitable, hexane, is preferred.

Alternatively, the wet cake (which typically contains about 30–50% solids) can be crumbled and extracted directly using polar solvents such as ethanol or isopropyl alcohol, or supercritical fluid extraction with solvents such as $CO_2$ or NO. Preferably, the cakes are crumbled prior to extraction. Advantageously, the present invention permits the economical use of supercritical fluid extraction techniques. McHugh, et al., *Supercritical fluid Extraction*, Butterworth (1986). Such techniques are known to those of skill in the art and include those presently applied, for example, to decaffeinate coffee beans. While the yields from both wet and dry extractions are similar, wet extraction generally is a more economical process.

Another aspect of the invention discloses a process for supplementing or altering the composition of commercially available infant formula so as to provide them with a PUFA composition more nearly like that typically contained in human breast milk. "Typical" as used herein refers to the average amounts of PUFAs measured. One of the advantages of the present invention is that, if desired, a nursing mother choosing to switch to formula can have her breast milk analyzed for PUFA content. Then, an additive for a commercially available formula which will supply comparable amounts of PUFAs can be specifically designed. Long chain PUFA-containing microbial oils from at least two microorganisms can be obtained and blended together to provide the desired composition. The blend then can be added to an infant formula. Preferably, an amount of the blend effective to provide an amount of the desired PUFAs substantially similar to that found in human breast milk will be provided.

Typically, human breast milk contain from about 0.5 to 0.6% of its fatty acid content as ARA, from about 0.15 to about 0.36% of its fatty acid content as DHA and from about 0.03 to about 0.13% of its fatty acid content as EPA. Thus, a preferred ratio of ARA:DHA:EPA is from about 5:1:1 to about 20:10:1 respectively. Amounts of oils providing approximately these ratios of PUFAs can be determined without undue experimentation by those of skill in the art.

In a preferred embodiment, the microbial oils include ARASCO and DHASCO and EPASCO or any combination thereof. It is also preferred to use oil from microbes of the genera Mortierella, Pythium, Crypthecodinium, and Nitzschia or any combination thereof. Particularly preferred species from these genera are *M. alpina, P. insidiosum, C. cohnii* and *N. alba.* This preferred embodiment would provide an acceptable alternative for vegetarians, including breast-feeding or pregnant vegetarian women.

If desired, fish oil can be blended, or mixed, with any combination of, or individual, microbial oil to produce a composition which, when subsequently added to infant formula will alter the PUFA content thereof in a desirable manner. Such a composition would not be suitable for a strict vegetarian intake. A preferred fish oil is specially processed Menhaden Oil (produced by Zapata Hayne, Inc.) which typically contains about 9% DHA. Of course, other fish oils also can be used.

When DHASCO is to be blended with ARASCO, and no other PUFA-containing oils are to be utilized., it is desirable to blend sufficient amounts of the oils to provide from about 1 to about 5 parts DHA with from about 2 to about 12 parts ARA. A most preferred ratio of DHA to ARA is 1:3 respectively.

As another example, Menhaden fish oil, as noted above, typically contains about 9% by weight DHA ARASCO typically contains about 20–40% by weight ARA. DHASCO typically contains about 25–40% by weight DHA. It has been found that a blend of 1 part Menhaden oil containing about 9% by weight DHA with 10 parts ARASCO containing about 33% by weight ARA and 3 parts DHASCO containing about 35% by weight DHA, when added to infant formula, causes the infant formula to closely approximate the ARA and DHA content of human breast milk. Other ratios can be readily calculated.

In another embodiment of the present invention is disclosed a process for making a supplement for infant formula or baby food which entails blending a DHA-containing oil with a GLA-containing oil. It is to be understood that, in general, any combination of GLA-EPA-ARA-or DHA-containing oils, with or without fish oil, can be used. The source of the GLA can be a vegetable oil, such as primrose, black currant or borage oil, or a microbial oil such as the oil from *Mucor javonicus* or *Mortierella isabellina*, for example. Table 1 sets forth the GLA composition of such oils. In a preferred aspect of this embodiment, about 1 part of Menhaden oil containing about 9% DHA, about 4 parts of GLA-containing oil containing about 18% GLA from black currant seed, and about 1 part of DHASCO containing about 33% DHA are blended together. Other ratios can be selected as desired.

TABLE 1

Fatty acids of commercially available oils containing GLA
(from Lawson and Hughes, 1988 and Suzuki, 1989)
Relative % of total acyl groups in oil from:

| Fatty acyl group | Mucor javanicus* | Mortierella isabellina** | Evening Primrose | Black-currant | Borage |
|---|---|---|---|---|---|
| 14:0 | 1.0 | 0.7 | — | — | — |
| 14:1 | 0.1 | — | — | — | — |
| 16:0 | 18.6 | 27.2 | 5.9 | 6.9 | 10.7 |
| 16:1 | 1.0 | 0.9 | — | — | — |
| 18:0 | 7.1 | 5.7 | 1.8 | 1.3 | 3.0 |
| 18:1 | 39.9 | 43.9 | 7.5 | 10.8 | 15.4 |
| 18:2 | 8.9 | 12.0 | 74.8 | 46.7 | 38.1 |
| γ-18:3(ω6) | 17.9 | 8.3 | 9.3 | 15.9 | 24.8 |
| α-18:3(ω3) | — | — | — | 13.0 | — |
| 18:4(ω3) | — | — | — | 2.9 | — |
| 20:0 | — | 0.6 | — | — | — |
| 20:1(ω9) | — | — | — | — | 4.0 |
| 22:0 | — | 0.1 | — | — | — |
| 22:1(ω9) | — | 0.2 | — | — | 2.2 |
| 24:0 | 0.6 | — | — | — | — |

*Produced by J. & E. Sturge Ltd., Selby, N. Yorks., U.K.
**Produced by Idemitzu Petro Chemical Co. Ltd., Tokyo, Japan.
Lawson - Lipids 23:313-317 (1988)
Suzuki - In Biotechnology for the Fats and Oils Industry p.110–116. Amer Oil Chem. Soc. Press (1989).

A composition including a blend of any combination of the above-described microbial oils with or without either, or both, fish oil and vegetable oil is another aspect of the present invention. While the composition includes any ratios of the oils, the ratios previously described are preferred.

In another preferred embodiment, the composition serves as a nutritional supplement. Typically, such supplements are encapsulated, such as in gelatin capsules. Such capsules provide an easy form of administration to persons having a need for supplementation, such as pregnant or nursing women. However, parenteral administration is a viable option and in one embodiment the composition comprises the fat component of a total parenteral nutritional formula. Such formulas are known and commercially available.

As will be understood, the composition of the present invention is particularly useful as a dietary supplement for pregnant or nursing women. Vegetarian women, in particular, may require increased amounts of DHA and ARA, yet have been precluded from obtaining such in the past because the only available sources were animal.

The invention having been previously described in general, reference is now had to the following non-limiting examples for illustrative purposes only.

EXAMPLES

Example 1

Preparation of *P. insidiosum* lipid

In an 80 liter (gross volume) fermentor, 51 liters of tap water, 1.2 kg glucose, 240 grams of yeast extract and 15 ml of MAZU 210S ® antifoam were combined. The fermentor was sterilized at 121° C. for 45 minutes. An additional 5 liters of condensate water were added during the sterilization process. The pH was adjusted to 6.2, and approximately 1 liter of inoculum (at a cell density of 5–10 g/l ) of .Pythium insidiosum (ATCC #28251) then was added. The agitation rate was adjusted to 125 RPM (250 cm/sec tip speed) and the aeration rate was set a 1 SCFM (standard cubic feet per minute). At hour 24 in the operation the aeration rate as increased to 3 SCFM. At hour 28 an additional 2 liters of 50% glucose syrup (1 kg glucose) were added. At hour 50 the fermentor was harvested, resulting in a yield of about 2.2 kg wet weight (approximately 15 g dry weight) per liter. Harvested biomass was squeezed to a high solids cake (50% solids) on a suction filter before freeze drying. The dried biomass was ground with a mortar and pestle and extracted with 1 liter of hexane per 200 grams of dry biomass at room temperature under continuous stirring for 2 hours. The mixture then was filtered and the filtrate evaporated to yield about 5–6 grams of crude oil per 100 grams of dry biomass. The biomass then was reextracted with 1 liter of ethanol per 20 grams of dry biomass for 1 hour at room temperature, filtered, and the solvent evaporated yielding an additional 22 grams of crude oil per 100 grams of dry biomass. The second fraction was predominantly phospholipids whereas the first fraction contained a mixture of phospholipids and triglycerides. The combined fractions produced an oil containing about 30–35% arachidonic acid and no detectable EPA.

Example 2

Preparation of *M. alpina* lipid

*Mortierella alpina* (ATCC #42430) was grown in a 2 liter shake flask containing 1 liter of tap water and 20 grams of potato dextrose medium. The flask was under constant orbital agitation and was maintained at 25° C. for seven days. After harvesting by centrifugation, the biomass was freeze dried yielding about 8 grams of lipid-rich mycelia. The mycelia was extracted using hexane as in example #1 and about 2.4 g of crude oil resulted. This oil contains about 23% arachidonic acid.

Example 3

Into a 30-liter working volume STF was loaded a medium of one quarter strength artificial seawater. Six liters of IO were combined with 18 liters of tap water. The fermentor containing the medium was sterilized and cooled to 28° C. Four hundred ml of concentrated YE (455 g/l ), 900 ml of glucose syrup (400 g/l) and one liter of inoculum from a seed fermentor containing about $2 \times 10^7$ *C. cohnii* cells/ml or a biomass of 20 g/liter (yielding a final concentration of about $10^5$ cells/ml of a biomass of about 700 mg/liter), were added to the medium. The *C. cohnii* cells, designated MK8840, were obtained from the American Type Culture Collection as ATCC 40750. Agitation was set at 120 cm/sec tip speed and aeration was set at 1 VVM (30 liters per minute). Additional glucose syrup (900 ml) was added after 30 hours and another 4.2 liters over the next 42 hours. Thus 6 liters of glucose syrup were added in total. Concentrated YE solution (400 ml) was added at hour 6 another 1.2 liters were added over the next 48 hours until a total of 2.0 liters had been added. To maintain the D.O. at greater than 20%, at 24 hours the agitation tip speed was increased to 150 cm/sec and at 48 hours to 160 cm/sec. At 72 hours, the tip speed was increased to 200 cm/sec and the culture was permitted to grow for an additional time sufficient to convert the final charge of glucose into cellular oil. The culture was then harvested by centrifugation with the cell pellet retained. The harvested pellet of cells was frozen and dried (lyophilized) to about a 4% moisture content. Hexane (2.8 liters) was added to the dried biomass and stirred in a glass kettle for 1.5 hours at 50° C. A rotary evaporate was used to remove the hexane, producing about 175 g of crude DHA-containing oil.

Example 4

Preparation of Oil Mix #1 and addition to infant formula

The first mixture represents a totally vegetarian source of an arachidonic and docosahexaenoic acid supplement. This supplement would be considered acceptable to persons restricted to a vegetarian diet. Sanders et al. (*Amer. J. Clin. Nutr.* 31:805; 1978) have reported that the DHA levels in the breast milk of vegetarian mothers are depressed. Enteral supplementation of a blend of DHA single cell oil and ARA single cell oil will elevate the serum and, hence, breast milk levels of DHA to that of omnivorous mothers. This blend is prepared by mixing one part DHASCO containing about 35% DHA (obtained from *Crypthecodinium cohnii* as described in Example 3 and deposited with the American Type Culture Collection in Rockville, Md. (ATCC) having accession number 40750) with three parts ARASCO containing about 33% ARA (obtained from *Pythium insidiosum* as described in Example 2 and on deposit with the ATCC, having accession number 28251). The resulting mixture, or blend, has the fatty acid composition shown in Table 2. The blend is mixed in a ratio of one part blend to forty parts of the oils regularly in infant formula, typically about 2.8–3.0 grams per 100 ml of formula. At a normal fat content of 30 g fat per liter of Similac ® infant formula, this corresponds to the addition of 750 mg per liter of prepared formula. This supplement provides ARA and DHA levels equivalent to human breast milk.

TABLE 2

Composition of a blend of DHA oil and ARA oil in proportions of 1:3 by weight.

| Fatty Acid | oil mix #1 | Infant formula | formula + mix #1 | breast milk |
|---|---|---|---|---|
| 8:0 + 10:0 | 0.00 | 41.8 | 40.78 | 1.74 |
| 12:0 + 14:0 | 13.63 | 20.7 | 20.53 | 14.95 |
| 16:0 | 17.05 | 6.8 | 7.05 | 19.82 |
| 16:1 | 7.88 | 0.2 | 0.39 | 3.20 |
| 18:0 | 0.00 | 2.3 | 2.24 | 5.91 |
| 18:1 | 7.48 | 10.0 | 9.94 | 34.82 |
| 18:2 n6 | 7.20 | 17.4 | 17.15 | 16.00 |
| 18:3 n3 | 2.25 | 0.9 | 0.93 | 0.62 |
| 18:3 n6 | 4.50 | — | 0.11 | 0.00 |

TABLE 2-continued

Composition of a blend of DHA oil and ARA oil in proportions of 1:3 by weight.

| Fatty Acid | oil mix #1 | Infant formula | formula + mix #1 | breast milk |
|---|---|---|---|---|
| 20:1 | — | 0.1 | 0.10 | 1.10 |
| 20:2 n6 | — | — | 0.00 | 0.61 |
| 20:3 n6 | — | — | 0.00 | 0.42 |
| 20:4 n6 | 24.75 | — | 0.60 | 0.59 |
| 20:5 n3 | — | — | 0.00 | 0.03 |
| 22:1 | — | — | 0.00 | 0.10 |
| 22:4 n6 | — | — | 0.00 | 0.21 |
| 22:5 n6 | — | — | 0.00 | 0.22 |
| 22:6 n3 | 8.98 | — | 0.22 | 0.19 |

Example 5

Preparation of Oil Mix #2 and addition to infant formula

This mixture represents a totally vegetarian source of long chain PUFAs and would be considered acceptable to persons restricted to a vegetarian diet. This blend is prepared by mixing three parts DHASCO containing about 35% DHA (obtained from *Crypthecodinium cohnii* as described in Example 3 with ten parts ARASCO containing about 33% ARA (obtained from *Pythium insidiosum* as described in Example 2 filed concurrently herewith) and five parts EPASCO containing about 5% EPA (obtained from *N. alba* on deposit with the ATCC as described in Example 1. The resulting mixture, or blend, has the fatty acid composition shown in Table 3. The blend is mixed in a ratio of one part blend to thirty parts of the oils regularly in infant formula. At a normal fat content of 30 g fat per liter of Similac ® infant formula, this would correspond to the addition of one gram per liter of prepared formula. This supplement provides ARA, DHA and EPA levels equivalent to human breast milk.

TABLE 3

Composition of a blend of DHA oil, ARA oil and EPA oil in proportions of 3:10:5 by weight.

| Fatty Acid | oil mix #2 | Infant formula | formula + mix #2 | breast milk |
|---|---|---|---|---|
| 8:0 + 10:0 | 0.00 | 41.8 | 40.45 | 1.74 |
| 12:0 + 14:0 | 16.64 | 20.7 | 20.57 | 14.95 |
| 16:0 | 21.61 | 6.8 | 7.28 | 19.82 |
| 16:1 | 6.55 | 0.2 | 0.40 | 3.20 |
| 18:0 | 0.28 | 2.3 | 2.23 | 5.91 |
| 18:1 | 12.91 | 10.0 | 10.09 | 34.82 |
| 18:2 n6 | 5.87 | 17.4 | 17.03 | 16.00 |
| 18:3 n3 | 1.88 | 0.9 | 0.93 | 0.62 |
| 18:3 n6 | 3.48 | — | 0.11 | 0.00 |
| 20:1 | — | 0.1 | 0.10 | 1.10 |
| 20:2 n6 | — | — | 0.00 | 0.61 |
| 20:3 n6 | 0.19 | — | 0.01 | 0.42 |
| 20:4 n6 | 18.52 | — | 0.60 | 0.59 |
| 20:5 n3 | 0.76 | — | 0.02 | 0.03 |
| 22:1 | — | — | 0.00 | 0.10 |
| 22:4 n6 | 0.11 | — | 0.00 | 0.21 |
| 22:5 n6 | — | — | 0.00 | 0.22 |
| 22:6 n3 | 6.24 | — | 0.20 | 0.19 |

Example 6

Preparation of Oil Mix #3 and addition to infant formula

This mixture is a blend of ARASCO with fish oils. Oil mixture #3 is prepared by adding one part specially processed Menhaden Oil (Zapata Hayne Inc.) containing about 9% DHA to one part of ARASCO, obtained from *Pythium insidiosum* as described previously containing about 33% ARA. The resultant fatty acid composition is shown in Table 4. This blend is mixed in a ratio of one part blend to thirty parts of the oils regularly in infant formula. At a normal fat content of 30 g fat per liter of infant formula, this corresponds to the addition of 1 gram per liter of prepared formula. This supplement provides ARA and DHA levels equivalent to human breast milk, but the EPA levels are about eight-fold higher than those in breast milk.

TABLE 4

Composition of a blend of SPMO* and ARA oil in proportions of 1:1 by weight.

| Fatty Acid | oil mix #3 | Infant formula | formula + mix #3 | breast milk |
|---|---|---|---|---|
| 8:0 + 10:0 | 0.0 | 41.8 | 40.45 | 1.74 |
| 12:0 + 14:0 | 10.2 | 20.7 | 20.36 | 14.95 |
| 16:0 | 15.5 | 6.8 | 7.08 | 19.80 |
| 16:1 | 11.5 | 0.2 | 0.56 | 3.20 |
| 18:0 | 1.41 | 2.3 | 2.27 | 5.91 |
| 18:1 | 8.79 | 10.0 | 9.96 | 34.82 |
| 18:2 n6 | 5.57 | 17.4 | 17.02 | 16.00 |
| 18:3 n3 | 2.31 | 0.9 | 0.95 | 0.62 |
| 18:3 n6 | 3.00 | — | 0.10 | 0.00 |
| 20:1 | 0.78 | 0.1 | 0.12 | 1.10 |
| 20:2 n6 | 0.00 | — | 0.00 | 0.61 |
| 20:3 n6 | 0.00 | — | 0.00 | 0.42 |
| 20:4 n6 | 17.52 | — | 0.57 | 0.59 |
| 20:5 n3 | 7.76 | — | 0.25 | 0.03 |
| 22:1 | 0.00 | — | 0.00 | 0.10 |
| 22:4 n6 | 0.00 | — | 0.00 | 0.21 |
| 22:5 n6 | 1.21 | — | 0.04 | 0.22 |
| 22:6 n3 | 4.57 | — | 0.15 | 0.19 |

*Specially Processed Menhaden Oil.

Example 4

Preparation of Oil Mix #4 and addition to infant formula

Oil mixture #4 was developed to utilize GLA in place of arachidonic acid. This blend was prepared by mixing one part specially prepared Menhaden oil containing about 9% DHA (Zapata Hayne Inc.) with four parts black currant seed oil containing about 18% GLA and one part DHASCO containing about 35% DHA. The resultant fatty acid composition is shown in Table 5. This blend is mixed in a ratio of one part blend to forty parts of the oils regularly in infant formula. At a normal fat content of 30 g fat per liter, this would correspond to the addition of 750 mg per liter of prepared formula. This supplement provides EPA and DHA levels equivalent to human breast milk. The ARA levels are about one tenth the level in human breast milk. However, the GLA levels are twenty to fifty times higher than the GLA levels in breast milk which typically are minute.

TABLE 5

Composition of a blend of SPMO, BCO and DHA oil in proportions of 1:4:1 by weight.

| Fatty Acid | oil mix #4 | Infant formula | formula + mix #4 | breast milk |
|---|---|---|---|---|
| 8:0 + 10:0 | 0.0 | 41.8 | 40.78 | 1.74 |
| 12:0 + 14:0 | 4.83 | 20.7 | 20.31 | 14.95 |
| 16:0 | 11.86 | 6.8 | 6.92 | 19.80 |
| 16:1 | 2.09 | 0.2 | 0.25 | 3.20 |
| 18:0 | 1.34 | 2.3 | 2.28 | 5.91 |
| 18:1 | 10.98 | 10.0 | 10.02 | 34.82 |
| 18:2 n6 | 31.39 | 17.4 | 17.74 | 16.00 |
| 18:3 n3 | 8.94 | 0.9 | 1.10 | 0.62 |
| 18:3 n6 | 10.60 | — | 0.26 | 0.00 |
| 20:1 | 0.26 | 0.1 | 0.10 | 1.10 |
| 20:2 n6 | — | — | 0.00 | 0.61 |
| 20:3 n6 | — | — | 0.00 | 0.42 |
| 20:4 n6 | 0.34 | — | 0.06 | 0.59 |

TABLE 5-continued

Composition of a blend of SPMO, BCO and DHA oil in proportions of 1:4:1 by weight.

| Fatty Acid | oil mix #4 | Infant formula | formula + mix #4 | breast milk |
|---|---|---|---|---|
| 20:5 n3 | 2.59 | — | 0.00 | 0.03 |
| 22:1 | — | — | 0.00 | 0.10 |
| 22:4 n6 | — | — | 0.00 | 0.21 |
| 22:5 n6 | 0.40 | — | 0.01 | 0.22 |
| 22:6 n3 | 7.51 | — | 0.18 | 0.19 |

Example 5

Preparation of Oil Mix #5 and addition to infant formula

Oil mixture #5 was developed to best approximate the composition of DHA, ARA and EPA of human breast milk. This oil blend was prepared by mixing one part specially prepared Menhaden oil containing about 9% DHA (Zapata Hayne Inc.) with ten parts of ARASCO containing about 33% ARA and three parts DHASCO containing about 35% DHA. The resultant fatty acid composition is shown in Table 6. This blend is mixed in a ratio of one part blend to forty parts of the oils regularly in infant formula. At a normal fat content of 30 g fat per liter of infant formula, this corresponds to the addition of 750 mg per liter of prepared formula. This supplement provides EPA, DHA and ARA levels substantially equivalent to those levels in human breast milk.

TABLE 6

Composition of a blend of SPMO, ARA oil and DHA oil in proportions of 1:10:3 by weight.

| Fatty Acid | oil mix #5 | Infant formula | formula + mix #5 | breast milk |
|---|---|---|---|---|
| 8:0 + 10:0 | 0.00 | 41.8 | 40.78 | 1.74 |
| 12:0 + 14:0 | 13.14 | 20.7 | 20.52 | 14.95 |
| 16:0 | 16.83 | 6.8 | 7.04 | 19.80 |
| 16:1 | 8.39 | 0.2 | 0.40 | 3.20 |
| 18:0 | 0.20 | 2.3 | 2.25 | 5.91 |
| 18:1 | 7.66 | 10.0 | 9.94 | 34.82 |
| 18:2 n6 | 6.97 | 17.4 | 17.15 | 16.00 |
| 18:3 n3 | 2.26 | 0.9 | 0.93 | 0.62 |
| 18:3 n6 | 0.25 | — | 0.01 | 0.00 |
| 20:1 | 0.11 | 0.1 | 0.10 | 1.10 |
| 20:2 n6 | — | — | 0.00 | 0.61 |
| 20:3 n6 | — | — | 0.00 | 0.42 |
| 20:4 n6 | 23.72 | — | 0.58 | 0.59 |
| 20:5 n3 | 1.11 | — | 0.03 | 0.03 |
| 22:1 | — | — | 0.00 | 0.10 |
| 22:4 n6 | — | — | 0.00 | 0.21 |
| 22:5 n6 | 0.17 | — | 0.00 | 0.22 |
| 22:6 n3 | 8.35 | — | 0.20 | 0.19 |

We claim:

1. A process for supplementing infant formula with DHA and ARA which comprises:
   (a) preparing an oil blend consisting essentially of a microbial oil enriched in DHA and a microbial oil enriched in ARA, wherein the DHA and ARA are in the form of triglycerides and the oils are blended to provide a ratio of about 2 to 12 parts ARA and about 1 to 5 parts DHA and the oil blend further provides an EPA:ARA ratio of about 1 part EPA to from about 5 to about 20 parts ARA, and
   (b) adding said oil blend to said infant formula in sufficient amounts that the amounts of DHA, ARA and EPA in said formula are comparable to the amounts of DHA, ARA and EPA in human breast milk.

2. A process in accordance with claim 1, wherein the ARA-containing oil comprises at least 20% ARA.

3. A process in accordance with claim 1, wherein the DHA-containing oil comprises at least about 25% DHA.

4. A process in accordance with claim 1, wherein the DHA-containing oil and the ARA-containing oil are added to the infant formula to provide a ratio of ARA:DHA ranging from about 3:1 to about 2:1.

5. A process in accordance with claim 4, wherein the DHA-containing oil and the ARA-containing oil are added to the infant formula to provide a ratio of ARA:DHA of about 2:1.

6. A process in accordance with claim 1, wherein said ARA-containing oil is obtained by a process comprising cultivating *Pythium insidiosum* or *Mortierella alpina* under conditions which will induce the production of an oil enriched in ARA.

7. A process in accordance with claim 1, wherein said DHA-containing oil is obtained by cultivating a DHA-producing species of Crypthecodinium.

8. A process for supplementing infant formula with DHA and ARA which consists essentially of blending a triglyceride oil enriched in DHA and a triglyceride oil enriched in ARA, wherein the oils are blended to provide an ARA:DHA:EPA ratio of from about 5 parts ARA and 1 part DHA to about 20 parts ARA and 10 parts DHA to about 1 part EPA, and adding said blend to infant formula in amounts sufficient to provide the infant formula with DHA, ARA and EPA in amounts comparable to the amounts of DHA, ARA and EPA in human breast milk.

9. A process for supplementing infant formula with DHA and ARA which consists essentially of:
    (a) obtaining a microbial oil enriched in DHA and blending it with a microbial oil enriched in ARA, wherein the DHA and ARA are in the form of triglycerides and the oils are blended to provide a ratio of about 2 to 12 parts ARA and about 1 to 5 parts DHA and the oil blend is free of EPA, and
    (b) adding said oil blend to said infant formula in sufficient amounts that the amounts of DHA and ARA in said formula are comparable to the amounts of DHA and ARA in human breast milk.

10. A composition consisting essentially of a blend of a microbial oil enriched in DHA and a microbial oil enriched in ARA, wherein said DHA and ARA are in the form of triglycerides and the oils are blended to provide an ARA:DHA:EPA ratio of from about 5 parts ARA and 1 part DHA to about 20 parts ARA and 10 parts DHA to about 1 part EPA.

11. A composition in accordance with claim 10, wherein the microbial oil enriched in DHA comprises at least about 25% DHA.

12. A composition in accordance with claim 10, wherein the microbial oil enriched in ARA comprises at least about 20% ARA.

13. A composition consisting essentially of a blend of a microbial oil enriched in DHA and a microbial oil enriched in ARA, wherein the oils are blended to provide a ratio of about 2 to 12 parts ARA and about 1 to 5 parts DHA.

14. A composition in accordance with claim 13, wherein the oils are blended to provide a ratio of ARA:DHA of about 2:1.

15. A composition in accordance with claim 13, wherein the amount of EPA is about one twentieth or less the amount of ARA.

16. A composition in accordance with claim 13, wherein the oil enriched in ARA was produced by cultivating *Pythium insidiosum* or *Mortierella alpina* under conditions which will induce the production of an oil enriched in ARA.

17. A composition in accordance with claim 13, wherein the oil enriched in DHA was produced by cultivating a DHA-producing species of Crypthecodinium under DHA-producing conditions.

18. A composition comprising a blend of triglyceride oils, wherein said blend consists essentially of ARA, DHA and EPA in a ratio of about 20:10:1 to about 5:1:1.

19. A composition comprising a blend of a microbial triglyceride oil enriched in ARA and a microbial triglyceride oil enriched in DHA, wherein the microbial triglyceride oils are provided in amounts to provide a ratio of about 2 to 12 parts ARA and about 1 to 5 parts DHA and said oils further are free of EPA.

20. Infant formula comprising a blend of a microbial oil enriched in DHA and a microbial oil enriched in ARA, wherein the DHA and ARA are in the form of triglycerides and the oils are blended to provide a ratio of about 2 to 12 parts ARA and about 1 to 5 parts DHA, the amount of DHA-containing oil and the amount of ARA-containing oil are sufficient to provide amounts of ARA and DHA comparable to the amounts of DHA and ARA in human breast milk and the formula further comprises EPA in a maximum amount of about one twentieth the amount of ARA.

21. Infant formula consisting essentially of a blend of a microbial oil enriched in DHA and an oil enriched in GLA, wherein the amount of the DHA-containing oil is sufficient to provide an amount of DHA comparable to the amount in human breast milk and the amount of the GLA-containing oil is sufficient to provide GLA in an amount that, upon administration of the formula to an infant, can be converted in the infant's body to an amount of ARA comparable to the amount of ARA obtainable from human breast milk.

22. Infant formula comprising DHA and ARA, wherein the DHA and ARA are in the form of triglycerides, the triglycerides are blended to provide a ratio of about 2 to 12 parts ARA and about 1 to 5 parts DHA, and the amount of DHA-containing triglyceride and the amount of ARA-containing triglyceride are sufficient to provide amounts comparable to the amounts of DHA and ARA in human breast milk, wherein said formula is free of EPA.

* * * * *

(12) EX PARTE REEXAMINATION CERTIFICATE (7180th)
United States Patent
Kyle

(10) Number: US 5,374,657 C1
(45) Certificate Issued: Nov. 24, 2009

(54) MICROBIAL OIL MIXTURES AND USES THEREOF

(75) Inventor: David J. Kyle, Catonsville, MD (US)

(73) Assignee: Martek Corporation, Columbia, MD (US)

Reexamination Request:
No. 90/009,106, Apr. 14, 2008

Reexamination Certificate for:
Patent No.: 5,374,657
Issued: Dec. 20, 1994
Appl. No.: 07/944,739
Filed: Sep. 14, 1992

Related U.S. Application Data

(63) Continuation of application No. 07/645,457, filed on Jan. 24, 1991, now abandoned.

(51) Int. Cl.
*A61K 31/20* (2006.01)
*A61K 31/185* (2006.01)
*A61K 31/23* (2006.01)
*A61K 31/21* (2006.01)
*A23L 1/30* (2006.01)

(52) U.S. Cl. ........................ 514/547; 514/560
(58) Field of Classification Search ................. None
See application file for complete search history.

(56) References Cited

U.S. PATENT DOCUMENTS

| | | | |
|---|---|---|---|
| 2,611,706 A | 9/1952 | Bernhart et al. |
| 2,923,628 A | 2/1960 | Otto |
| 3,458,625 A | 7/1969 | Ensor et al. |
| 3,542,560 A | 11/1970 | Tomarelli et al. |
| 3,649,295 A | 3/1972 | Bernhart et al. |
| 4,058,594 A | 11/1977 | Williams |
| 4,216,236 A | 8/1980 | Mueller et al. |
| 4,282,265 A | 8/1981 | Theuer |
| 4,303,692 A | 12/1981 | Gaull |
| 4,513,008 A | 4/1985 | Recivi et al. |
| 4,526,793 A | 7/1985 | Ingenbleek et al. |
| 4,526,902 A | 7/1985 | Rubin |
| 4,544,559 A | 10/1985 | Gil et al. |
| 4,614,663 A | 9/1986 | Rule |
| 4,670,285 A | 6/1987 | Clandinin et al. |
| 4,681,896 A | 7/1987 | Horrobin |
| 4,703,060 A | 10/1987 | Traitler et al. |
| 4,752,618 A | 6/1988 | Mascioli et al. |
| 4,780,456 A | 10/1988 | Pistolesi et al. |
| 4,792,418 A | 12/1988 | Rubin |
| 4,810,497 A | 3/1989 | Horrobin |
| 4,820,731 A | 4/1989 | Mascioli et al. |
| 4,826,877 A | 5/1989 | Stewart et al. |
| 4,843,095 A | 6/1989 | Rubin |
| 4,851,343 A | 7/1989 | Herbert et al. |
| 4,868,001 A | 9/1989 | Maruta |
| 4,874,603 A | 10/1989 | Fratzer |
| 4,874,629 A | 10/1989 | Chang et al. |
| 4,876,107 A | 10/1989 | King et al. |
| 4,911,944 A | 3/1990 | Holub |
| 4,920,098 A | 4/1990 | Cotter et al. |
| 4,938,984 A | 7/1990 | Traitler et al. |
| 4,960,795 A | 10/1990 | Salte et al. |
| 4,963,385 A | 10/1990 | Antrim et al. |
| 5,013,569 A | 5/1991 | Rubin |
| 5,116,871 A | 5/1992 | Horrobin |
| 5,120,760 A | 6/1992 | Horrobin |
| 5,130,242 A | 7/1992 | Barclay |
| 5,198,468 A | 3/1993 | Horrobin |
| 5,204,250 A | 4/1993 | Shinmen et al. |
| 5,234,702 A | 8/1993 | Katz et al. |
| 5,338,673 A | 8/1994 | Thepenier et al. |
| 5,374,657 A | 12/1994 | Kyle |
| 5,397,591 A | 3/1995 | Kyle et al. |
| 5,407,957 A | 4/1995 | Kyle et al. |
| 6,448,055 B1 | 9/2002 | Shimizu et al. |

FOREIGN PATENT DOCUMENTS

| | | |
|---|---|---|
| DE | 3603000 | 8/1987 |
| DE | 3920679 | 1/1991 |
| EP | 0092085 | 3/1986 |
| EP | 0223960 | 6/1987 |
| EP | 0231904 | 8/1987 |
| EP | 0269351 | 6/1988 |
| EP | 0276541 | 8/1988 |
| EP | 0276982 | 8/1988 |
| EP | 0296751 | 12/1988 |
| EP | 332423 | 9/1989 |
| EP | 0404058 | 12/1990 |
| EP | 0 515 460 B1 | 4/1991 |
| EP | 0404058 | 12/1994 |
| EP | 0957173 | 11/1999 |
| EP | 1642983 | 4/2006 |
| GB | 1446431 | 8/1976 |
| JP | 62/79732 | 4/1987 |
| JP | 63 90598 | 4/1988 |
| JP | 01/038007 | 2/1989 |
| JP | 01/080250 | 3/1989 |
| JP | 01/132371 | 5/1989 |
| JP | 196255 | 8/1989 |
| JP | 01/196255 | 8/1989 |
| JP | 01/215245 | 8/1989 |
| JP | 01/304892 | 12/1989 |
| JP | 02/257835 | 10/1990 |

(Continued)

OTHER PUBLICATIONS

Aaronson, et al. Microalgae as a Source of Chemicals and natural Products, Algae Biomass, 1980, pp. 575–601, Shelef, et al. eds., Elsevier/North–Holland Biomedical Press.

Ackman, Problems in Fish Oils and Concentrates, Fats for the Future, 1989, Chp. 13, pp. 189–200, Combie ed.

Agency Response Letter GRAS Notice No. GRN 00109 (Annex C to D49).

Ahem, Tim, J.; Katoh, Shigeo and Eizo Sada. *Arachidonic Acid Production by the Red Alga Porphyridium cruentum*, Biotechnology and Bioengineering, 1983, 25:1057–1070.

(Continued)

*Primary Examiner*—Evelyn Huang

(57) ABSTRACT

The present invention relates to compositions including blends of microbial oils, methods of using such compositions, particularly as supplements for infant formula, and methods of increasing the amount of long chain polyunsaturated fatty acids in infant formula.

FOREIGN PATENT DOCUMENTS

| | | |
|---|---|---|
| JP | 63 90598 | 4/1998 |
| WO | WO 89/00606 | 1/1989 |
| WO | WO 90/04391 | 5/1990 |
| WO | WO 90/13656 | 11/1990 |
| WO | WO 91/07498 | 5/1991 |

OTHER PUBLICATIONS

AKU Strain List, 1990, p. 27.

Algae and Seaweed. Rodophyta (Red Algae) & Phaeophyta (Brown Algae) "Seaweed Site" 'http://seaweed.ucg.ie' © 1995–2003 Michael D. Guiry/Seaweed Home Page/Last modified Jan. 22, 2003.

Alternative Medicine, Excerpt from www.usadrug.com, (article can supplement the excerpt).

Amano et al., Chemotaxonomic Significance of Fatty Acid Composition in th eGenus Mortierella (Zygomycetes, Mortierellaceae), Mycotaxon, 1992, 94:257–265.

ANZFA Draft Assessment of Application A428 (Annex A to D429).

Ask Dr. Sears website (2006).

ATCC Letter, Jul. 13, 2004, 1 pg.

ATCC Catalog of Filamentous Fungi, 18$^{th}$ Ed., 1991, pp. 244–246, Jong et al. eds.

Bajpai, et al., Eicosapentaenoic Acid (EPA) Production by *Mortierella alpina* ATCC 32222, Appl. Biochem. Biotech., 1991, 31:267–272.

Beach, et al. Environmental Influences on the Docosahexaenoate Content of the Triacylglycerols and Phosphatidylcholine of a Heterotrophic, Marine Dinoflagellate, *Crypthecodinium cohnii*, Biochim. Biophys. Acta, 1973, 316:56–65.

Behrens, et al. Eicosapentaenoic Acid from Microalgae, Novel Microbial Products for Medicine and Agriculture, 1989, Chp. 28, pp. 253–259, Demain, et al. eds., Soc. for Industrial Microbiology.

Ben–Amotz, Chemical Profile of Selected Species of Microalgae with Emphasis on Lipids, J. Phycol. 1985, 21:72–81.

Bingham, Report on Analysis of Maeil Absolute Powdered Infant formula, Nov. 26, 2004, 8 pgs.

Biochemical Dictionary, Tokyo Biochemical Coterie, 1$^{st}$ Edition, 7$^{th}$ Printing (published Apr. 1, 1987).

Birch et al., Visual Acuity and the Essentiality of Docosahexaenoic Acid and Arachidonic Acid in the Diet in Term Infants, Pediatr. Res., 1998, 44(2):201–209.

Birch et al., A Randomized Controlled Trial of Long–Chain Polyunsaturated Fatty Acid Supplementation of Formula in Term Infants After Weaning at 6 wk of Age, Am. J. Clin. Nutr., 2002, 75:570–580.

Birch et al., Visual maturation of term infants fed long–chain polyunsaturated fatty acid–supplemented or control formula for 12 mo, Am. J. Clin. Nutr., 2005, 81: 871–879.

Bitman, et al. Comparison of the Lipid Composition of Breast Milk from Mothers of Term and Preterm Infants, Am. J. Clin. Nutr., 1983, 38:300–312.

Bjerve, et al. Omega–3 Fatty Acids: Essential Fatty Acids with Important Biological Effects and Serum Phospholipid Fatty Acids as Markers of Dietary ω3–Fatty Acid Intake, Am. J. Clin. Nutri., 1993, 57 (Suppl):801S–806S.

Blacks Medical Dictionary, 1992, 37$^{th}$ Ed., p. 375, Macpherson ed., A&C Black London.

Borowitzka, Fats, Oils and Hydrocarbons, Microalgae Biotech., 1988, Chp. 10, pp. 257–287, Borowitzka et al., eds., Cambridge Univ. Press.

Bourre, et al. Δ6 Desaturase in Brain and Liver During Development and Aging, Lipids, 1990, 25:354–356.

Boustani, et al. Enteral Absorption in Man of Eicosapentaenoic Acid in Different Chemical Forms, Lipids, 1987, 22:711–714.

Bracco, et al. Human Milk Lipids and Problems Related to Their Replacement, Extract from Annales Nestle, 1978, 40:55–81.

Carlson et al., Arachidonic acid status correlates with first year growth in preterm infants, Proc. Natl. Acad. Sci. USA, 1993, 90:1073–1077.

Carlson et al., Docosahexaenoic acid status of preterm infants at birth and following feeding with human milk or formula, Am. J. Clin. Nutr., 1986, 44:798–804.

Carlson, et al. Growth and Development of Very Low–Birthweight Infants in Relation to n–3 and n–6 Essential Fatty Acid Status, Essential Fatty Acids and Eicosenoids–Invited Papers form the Third International Congress, 1992, 1:192–196, Sinclair, et al. eds., American Oil Chem. Soc., Champaign, IL.

Carlson, et al. Long Term Docosahexaenoate (DHA) and Ecosapentaenoate (EPA) Supplementation of Preterm Infants: Effects on Biochemistry, Visual Acuity, Information Processing and Growth In Infancy, Inform, Apr. 1990, 1(4):306.

Carlson, Effect of Fish Oil Supplementation on the n–3 Fatty Acid Content of Red Blood Cell Membranes in Preterm Infants, Pediatri. Res., 1987, 21:507–510.

Carlson, Effect of Fish Oil Supplementation on the n–3 Fatty Acid Content of Red Blood Cell Membranes in Preterm Infants, Chem. Abst., 1987, 107:57830c.

Carlson et al., Visual–acuity development in healthy preterm infants: effect of marine–oil supplementation, Am J Clin Nutr 1993, 58:35–42.

Carlson et al., Effect of long–chain n–3 fatty acid supplementation on visual acuity and growth of preterm infants with and without bronchopulmonary dysplasia, Am. J. Clin. Nutr., 1996, 63:687–697.

Clandinin, et al. Long Chain Polyenoic Essential Fatty Acids in Human Milk: Are They of Benefit to the Newborn?, Composition and Physiological Properties of Human Milk, 1985, Schaub J. ed., Elsevier Science.

Clandinin et al., Growth and Development of Preterm Infants Fed Infant formulas Containing Docosahexaenoic Acid and Arachidonic Acid, J. Pediatr., Apr. 2005, pp. 461–468.

Cohen, Production of Eicosapentaenoic and Arachidonic Acids by the Red Alga *Porphyridium Cruentum*, World Conference on Biotechnology for the Fats and Oils Industry, 1988, pps 285–287, Applewhite, Thomas H. editor.

Cohen et al., The Effect of Temperature on Cell Concentration on the Fatty Acid Composition of Outdoor Cultures of *Porphyridium Cruentum*, Algal Biotechnology, pp. 421–429, T. Stadler et al. eds.

Davies, Yeast Oil From Cheese Whey—Process Development, Single Cell Oil, 1988, Chp. 4, pp. 99–145, Moreton ed., Longman Scientific & Technical/John Wiley & Sons, Inc. New York.

Food Standards Australia New Zealand, DHASCO and ARASCO Oils as Sources of Long–Chain polyunsaturated Fatty Acids in Infant Formula, A Safety Assessment, Jun. 2003, pp. 1–54 (with KR language abstract).

Dupont, Lipids, Present Knowledge in Nutrition, 1990, Chp. 7, pp. 56–66, Intl. Life Sci–Institute Nutrition Foundation, Washington, DC.

Effects of ω–3 Fatty Acid Supplemented Formula on the ω–3 and ω6 Fatty Acid Content of Red Blood Cell Membrane in Low Birth Weight Infants, J. Japan Pediatrics Soc., 1990, 94(2):224–234.

Garg et al., Effect of Dietary Cholesterol and/or ω3 Fatty Acids on Lipid Composition and $\Delta^5$–Desaturase Activity of Rat Liver Mocrosomes, J. Nutr., 1988, 118:661–668.

Gibson, A Lack of Correlation Between Linoleate and Arachidonate in Human Breast Milk, Communications, 1984, 19:469–471.

Giovannini, et al. N–3 Supplementation in Atopic Eczema of Children, Health Effects of Fish and Fish Oils, 1989, p. 591, Chandra ed., Arts Biomedical Publishers and Distributors, St. John's Newfoundland.

Göbbert et al., Abstracts for Poster Presentation: P–1 Microbial Transesterification of Sugar Corynomycolates, J. Am. Oil Chem. Soc., Sep. 1987, 64(9):1261–1262.

Hansson, et al. Effect of Culture Conditions on Mycelial Growth and Production of γ–Linolenic Acid by the Fungus *Mortierella ramanniana*, Appl. Microbiol. Biotechnol., 1988, 28:240–246.

Harel et al., Advanced DHA, EPA and ArA enrichment materials for marine aquaculture using single cell heterotrophs, Aquaculture, 2002, 213:347–362 (Annex B to D49).

Harrington, et al. The Polyunsaturated Fatty Acids of Marine Dinoflagellates, J. Protozool, 1970, 17(2):213–219.

Harris et al., Will dietary ω–3 fatty acids change the composition of human milk?, Am. J. Clin. Nutr., 1984, 40:780–785.

Harzer, et al. Changing Patterns of Human Milk Lipids in the Course of the Lactation and During the Day, Am. J. Clin. Nutr., 1983, 37:612–621.

Haskins et al., Steroids and the Stimulation of Sexual Reproduction of a Species of Pythium, CA J. Microbio., Dec. 24, 1964, 10:187–195.

Haug, Capillary Gas Chromatography of Fatty Acid Methyl Esters from Human Mile Lipid Subclasses, J. of Chromatography, 1983, 279:549–553.

Heird, Biological Effects and Safety Issues Related to Long–Chain Polyunsaturated Fatty Acids in Infants, Lipids, 1999, 34(2):207–213.

Henderson, et al. Lipid Composition and Biosynthesis in the Marine Dinoflagellate *Crypthecodinium cohnii*, Phytochem., 1988. 27:1679–1683.

Hoffman, et al., Impact of Early Dietary Intake and Blood Lipid Composition of Long–Chain Polyunsaturated Fatty Acids on Later Visual Development, J. Pediatr. Gatroenterol. Nutr., Nov. 2000, 31(5)540–553.

Hoffman et al., Visual Function in Breast–Fed Term Infants Weaned to Formula With or Without Long–Chain Polyunsaturates at 4 to 6 Months: A Randomized Clinical Trial, J. Pediatr. 2003, 142: 669–677.

Holman, Nutritional and metabolic interrelationships fatty acids, Federation Proceedings, 1964, 23:1062–1067.

Hori et al., Composition Analysis of Fats and oils Comprising of Polyunsaturated Fatty Acids by HPLC/FAB–MS II, Yukagaku, 1993, 42:989–955.

Ikeda et al., Digestion and lymphatic transport of eicosapentaenoic and docosahexaenoic acids given in the form of triacylglycerol, free acid and ethyl ester in rates, Biochim. Biophys. Acta, 1995, 1259:297–304.

Innis, et al. Plasma and Red Blood Cell Fatty Acids of Low–Birth–Weight Infants Fed Their mother's Expressed Breast Milk of Preterm–Infant Formula, Am. J. Clin. Nutr., 1990, 51:994–1000.

Innis et al., Docosahexaenoic acid and arachidonic acid enhance growth with no adverse effects in preterm infants fed formula, J. of Pediatr., May 2002, 140:547–554.

Ito, et al. Health Food Microcapsules Containing Unsaturated Fatty Acids for the Control of Cholesterol in Blood, Chem. Abst., 1985, 104:4865z.

Jensen, The Lipids in Human Milk, 1989, pp. 192–200, CRC Press, Boca Raton, FL.

Jensen, The Lipids in Human Milk, Prog. Lipid Res., 1996, 35(1):53–92.

Jensen et al., Lipids in Human Milk–Composition and Fat Soluble Vitamins, Textbook of Gastroenterology and Nutrition in Infancy, $2^{nd}$ Ed., 1989, Chp. 17, pp. 157–208, Lebenthal ed., Raven Press, Ltd., NY.

Johns et al., Fatty acid composition of ten marine algae from Australian waters, Phytochemistry, 1979, 18:799–802.

Kame, et al. Use of Fish Oil Fatty Acids (EPA and DHA) in Nutrition–Supplementing Foods and in Drugs, Chem. Abst., 1984, 100:66638d.

Kneebone et al., Fatty acid composition of breast milk from three racial groups from Penang, Malaysis, Am. J. Clin. Nutr., 1985, 41:765–769.

Kolestzko, Abstract from 3d Int. Congress on Polyunsaturated Fatty Acids in Adelaide, AU, 1992.

Koletzko, Effects of dietary long–chain polyunsaturated fatty acids on the essential fatty acid status of premature infants, Eur. J. Pediatr., 1989, 148:669–675.

Koletzko et al., Arachidonic Acid and Early Human Growth: Is there a Relation?, Ann. Nutr. Metab., 1991, 35:128–131.

Koletzko et al., Report of Workshop : Long chain polyunsaturated fatty acids (LC–PUFA) and perinatal development, Acta Paediatr, 2001, 90 :460–464.

Krokan et al., The enteral bioavailability of eioscapentaenoic acid and docosahexaenoic acid is a good from ethyl esters and from glyceryl esters in spite of lower hydrolytic rates by pancreatic lipase in vitro, Biochim. Biophys. Acta, 1993, 1168:59–67.

Kuwahara, Formation of Nicotinic Acid Ribonucleoside by an Enzyme Preparation and Growing Mycelium of *Aspergillus niger*, Agric. Bio. Chem., 1977, 41(4):625–629.

Kyle, Microbial Omega–3–Containing Fats and Oils for Food Use, Adv. Applied Biotech, 1991, 12:167–183.

Kyle, Market Application for Microalgae, JOACS, 1989, 66:648–651.

Kyle, et al., Chapter 16, Bioproduction of Docosahexaenoic Acid (DHA) by Microalgae, Ind. Appl. of Single Cell Oil, 1992, pp. 287–300, American Oil Chemists Society, Illinois.

Liu, et al. Increase in Plasma Phospholipid Docosahexaenoic and Eicosapentaenoic Acids as a Reflection of Their Intake and Mode of Administration, Pedatr. Res., 1987, 22:292–296.

Liu et al., In vitro hydrolysis of fungal oils: Distribution of Arachidonic Acid–containing Triacylglycerol molecular speices, JAOCS, 75, 4 (1998) 507–510.

List of Cultures, 1988, $8^{th}$ Ed. vol. 1 Institute of Fermentation, Osaka.

Lösel, Fungal Lipids, Microbial Lipids, 1988, vol. 1, Chapter 10, pp. 699–806.

Martek Biosciences Corporation, Life's DHA, Internet Resource (healthcare.martek.com), Feb. 22, 2008, 1 pg.

Moreton, Physiology of Lipid Accumulating Yeasts, Single Cell Oil, 1988, Chp. 1, pp. 1–11, Moreton ed., Longman Scientific & Technical/John Wiley & Sons, Inc. New York.

Morrison et al., Fatty Acid Composition of Milk Phospholipids II Sheep, Indian buffalo and Human Milk, Lipids, 1996, 2(12):178–182.

Murray et al., Standard Definition of Terms Relating to Mass Spectrometry, 2006, 4 pgs.

Nassar et al., The Influence of Dietary Manipulation with n–3 and n–6 Fatty Acids on Liver and Plasma Phospholipid Fatty Acids in Rats, Lipids, 1986, 21:652–656.

Nettleton, Omega–3 Fatty Acids in Early Human Development, Omega–3 Fatty Acids & Health, 1995, Chp. 6, pp. 249–275, Chapman & Hall, New York.

O'Connor et al., Growth and Development in Preterm infants Fed Long–Chain Polyunsaturated Fatty Acids: A Prospective, Randomized Controlled Trial, Pediatrics, Aug. 2001, 108(2):359–371.

Ohsugi et al., Biosynthesis of Biotin—Vitamers from unsaturated higher Fatty Acids by Bacteria, J. Nutr. Sci. Vitaminol., 1985, 31:253–263.

Olson et al., Arachidonic acid incorporation into lipids of term human amnion, Am. J. Obstet. Gynecol. 1988, 159:995–1001.

Packard, Macronutrients and Energy, Human Milk and Infant Formula, 1982, Chapter 1, pp. 7–49.

Packard, Infant Formula Composition, Formulation and Processing, Human Milk and Infant Formula, 1982, Chapter 6, pp. 140–175.

Pohl, et al. Fatty Acids and Lipids of Marine Algae and the Control of Their Biosynthesis by Environmental Factors, Marine Algae in Pharmaceutical Science, 1979, pp. 473–523, Hoppe, et al. eds., Walter de Grwyler, Berlin–New York.

Puppione, et al., Marine Mammals: Animal Models for Studying the Digestion and Transport of Dietary Fats Enriched in ω–3 Fatty Acids. Position Analyses of Milk Fat Triacylglycerol Molecules, Dietary ω–3 and ω–6 Fatty Acids, 1988, pp. 361–365, Galli et al. eds., Plenum Press.

Ratledge, The potential of Microorganisms for Oil Production—A Review of Recent Publication, Proc. World Conf. Emerging Technol. in the Fats Oils Industr., 1986, pp. 318–330 Baldwin ed., Am. Oil Chem Soc.

Ratledge, Lipids, Biotechnology, vol. 4, Chp. 7, pp. 186–196, Pape et al. eds., VCH, Weinheim, Germany.

Sanders, et al. Studies of Vegans: The Fatty Acid Composition of Plasma Choline Phosphoglycerides, Erythrocytes, Adipose Tissue, and Breast Milk, and some Indicators of Susceptibility to Ischemic Heart Disease in Vegans and Omnivore Controls, Am. J. Clin. Nutr., 1978, 31:805–813.

Sanders et al., The influence of different types of ω3 polyunsaturated fatty acids on blood lipids and platelet function in healthy volunteers, Clin. Sci., 1983, 64:91–99.

Sawada et al., Effect of Column Temperature on Improvement of Resolution in Separating Triglyceride Molecular Species Containing highly Unsaturated Fatty Acids by Reverse Phase High Preformance Liquid Chromatography, Nippon Suisan Gakkaishi, 1992, 58(7):1313–1317.

Schrijver et al., Effects of Dietary Long–Chain Fatty Acids on the Biosynthesis of Unsaturated Fatty Acids in the Rat, J. Nutr., 1982, 112: 619–626.

Shifrin, et al. Plytoplankton Lipids: Environmental Influences on Production and Possible Commercial Applications, Algae Biomass, 1980, pp. 627–645 Shelef et al. eds., Elsevier/North–Holland Biomedical Press.

Shifrin, Oils from Microalgae, Biotechnology for the Oils and Fats Industry, 1984, Chp. 14, pp. 145–162, Ratledge et al. eds., Am. Oil Chem. Soc., Champaign, IL.

Shimizu, Microbial Culture Collection of Laboratory of Applied Microbiology Kyoto University, May 1992, 1 pg.

Shimizu, et al. Production of Eicosapentaenoic Acid by Mortierella Fungi, J. Am. Oil Chem, Soc., 1988, 65(9):1455–1459.

Shimizu, et al. Production of C–20 Polyunsaturated Fatty Acids by Fungi, ISF–JOCS World Conference, 1988, 7 pgs.

Shimizu et al., Occurrence of a Novel Sterol, 24,25–Methylenecholest–5–en–3β–ol in *Mortierella alpina* 1S–4, Lipids, 1992, 27(6):481–483.

Shimizu, et al. Conversion of Linseed Oil to an Eicosapentaenoic Acid–Containing Oil by *Mortierella alpina* 1S–4 at Low Temperature, Appl. Microb. Biotechnol., 1989, 32:1–4.

Shimizu et al., Fungal Mycelia As A Novel Source of Eicosapentaenoic Acid: Activation of Enzyme(s) Involved in Eicosapentaenoic Acid Production at Low Temperature, Biochemical and Biophysical Research Communications, 1988, 150(1):335–341.

Shimizu et al., Microbial Production of Polyunsaturated Fatty Acids (Vitamin–F Group), Biotechnology of Vitamins, Pigments and Growth Factors, 1989, Chp. 7, pp. 106–121, Vandamme ed., Elsevier.

Shimizu et al., Production of Dietary and pharmacologically Important Polyunsaturated Fatty Acids by Microbiological Processes, Comments Agric. & Food Chem., 1990, 2(3):211–235.

Shinmen, et al. Production of Arachidonic Acid by *Mortierella* fungi: Selection of a Potent Producer and Optimization of Culture Conditions for Large–Scale Production, Appl. Microb. Biotech., 1989, 31:11–16.

Similac, Formula Compositions of Infant Formula Products Marketed in Korea, 4 pgs. (Internet site www.similac.co.kr/abbott/world/world1__1.jsp).

Simopoules, Omega 3 Fatty Acids, Health and Disease, 1990, p. 136, Lees et al. eds.

Simopolous et al., Workshop on the Essentiality of and Recommended Dietary Intakes of Omega–6 and Omega–3 Fatty Acids, ISSFAL Newsletter, 6(2):14–16, J. of Lipid Nutr., 1999, 8(2):128–135.

Simopolous et al., Workshop on the Essentiality of and Recommended Dietary Intakes of Omega–6 and Omega–3 Fatty Acids, J. Am. Coll. Nutr., 1999, 18(5):487–489.

Smith et al., Chemical marker for the differentiation of Group A and Group B Streptococci by Pyrolysis–Gas Chromatography–mass spectrometry, Anal. Chem., 1987, 59:1410–1413.

Sonnenborn, et al. Purification and Properties of the Fatty Acid Synthetase Complex from the Marine Dinoflagellate, *Crypthecodinium cohnii*, Biochem. Biophys. Acta, 1982, 712: 523–534.

Sridhar et al., Incorporation of Eicosapentaenoic and Docosahexaenoic Acids into Groundnut Oil by Lipase–Catalyzed Ester Interchange, JAOCS, Oct. 1992, 69(10):1041–1042.

Suntory, Arachidonic Acid–Containing Oil (SUNTGA 40S), 8 pgs.

Suzuki, Lipids of Fungi and Bacteria, Comprehensive Lipid Science, 1989, pp. 767–781, Kayama ed., Koseisha Koseikaku Co., Ltd.

Takashi, et al. Feeds Containing Highly Unsaturated Fatty Acids and Vitamin E for swine and production of pork using the feeds, Chem. Abst., 1991, 114: 41472w.

Totani, et al. The Filamentous Fungus *Mortierella alpina*, High in Arachidonic Acid, Lipids, 1987, 22(12):1060–1062.

Totani, et al, Production of Arachidonic Acid by *Mortierella alpina*, ISF–JOCS World Conference, 1988, pp. 993–999.

Totani et al., An Improved Method of Arachidonic Acid Production by *Mortierella alpina*, J. Jpn. Oil. Chem. Soc., 1987, 36:328–331.

Uchida et al., Continuous Production of NADP by Immobilized *Achromobacter aceris* Cells, Biotech. & Bioeng., 1978, 20:255–266.

U.S. Food and Drug Administration Subchapter B—Food for Human Consumption Part 107 Infant Formula (attachment of Patentee to letter of 25.2.05).

Vitamins, J. of the Vitamin Soc. of Japan, 1988, 62(8):439–445.

Volkman, et al. Fatty Acid and lipid Composition of 10 Species of Microalgae Used in Mariculture, J. Esp. Mar. Biol., 1989, 128:219–240.

Weaver, et al. The Effect of Positional Placement of EPA in Ingested Triglyceride on EPA Accumulation in Human Platelet and Plasma Phospholipides, Health Effects of Fish and Fish Oils, 1989, Chp. 39, pp. 581–589, Clandra ed., St. John's Newfoundland.

Weete et al., Fatty Acids and Sterols of Selected Hyphochytriomycetes and Chytridiomycetes, Exp. Mycology, 1989, 13:183–195.

Yahiro, Nutritional research for improvement of fat blending in infant formula, Research Report No. 90 of Institute of Snow Brand Milk Products Co. Ltd., 1990, 90:137–203.

Yamada, et al. Production of Dihomo–y–linolenic Acid, Arachidonic Acid and Eicosapentaenoic Acid by Filamentous Fungi, Ind. Appl. Single Cell Oils, 1992, Chp. 7, pp. 118–138.

Yamada, et al. Production of Arachidonic Acid and Eicosapentaenoic Acid by Microorganisms, Proc World Congr. Biotechnol. for Oils and Fats Industr., 1987, pp. 173–177, Applewhite, ed., Am. Oil Chem. Soc.

Yamada, et al. Biotechnological Processes for Production of Poly–Unsaturated Fatty Acids, J. Disp. Sci. & Tech., 1989, 10:561–579.

Yamada et al., Polyunsaturated Fatty Acid Produced by Microorganisms, Annual Report, Dai–Ichi Kogyo Seiyaku, Ltd., 1990, No. 466, pp. 2–7, Company Report of First Industrial Pharmaceutical Company (Japan).

Yamada et al., (Korean Language) Polyunsaturated Fatty Acid Produced by Microorganisms, Annual Report, Dai–Ichi Kogyo Seiyaku, Ltd., 1990, No. 466, pp. 2–7, Company Report of First Industrial Pharmaceutical Company (Japan).

Yazawa, Production of Lipid by Microorganism, Resource/Environment and Microorganism—Its new developments, Sagami Chem. Research Center, 1989, 5(6): 66–75.

Yeh, et al. Enrichment of (n–3) Fatty Acids of Suckling Rats by Maternal Dietary Menhaden Oil, Chem. Abstr., 1990, 113:38304d.

Yongmanitchai, et al. Omega–3 Fatty Acids: Alternative Sources of Production, Process Biochem., 1989, 24:117–125.

Yoshifusi, Introduction to the Patent Act, pp. 110–111.

Yoshifusi, Introduction to the Patent Act, pp. 164–165.

Carlson et al., First year growth of preterm infants fed standard compared to marine oil n–3 supplemented formulas, Lipids, 1992, 27(11):901–907.

Clandinin et al., Requirements of newborn infants for long chain polyunsaturated fatty acids, Acta. Paediatr. Scand. Suppl., 1989, 351:63–71.

Codex Alimentarius Commission, Codex Standard for Infant Formula, Stan 72–1981.

Crawford et al., Essential fayy acid requirement in infancy, Am. J. Clin. Nutr., 1978, 31:2181–2185.

Foote et al., Brain synaptosomal, liver, plasma, and red blood cell lipids in piglets fed exclusively on a vegetable–oil–containing formula with and without fish–oil supplements, Am. J. Clin. Nutr., 1990, 51(6):1001–1006.

Hrboticky et al., Effect of linoleic acid–rich infant formula feeding on brain synaptosomal lipid accretion and enzyme thermotropic behavior in the piglet, J. Lipid Res., 1989, 30(8):1173–1184.

Innis, Essential fatty acids in growth and development, Prog. Lipid Res., 1991, 30(1):39–103.

Koletzko et al., Fat content and fatty acid composition of infant formulas, Acta. Paediatr. Scand., 1989, 78:513–521.

Life Sciences Research Office (LSRO) Report, Assessment of Nutrient Requirements for Infant Formulas, J. Nutr., 1998, 128(11S):2105S–2106S.

Purvis et al., Fatty acid accretion during perinatal brain growth in the pig. A model for fatty acid accretion in human brain, Comp. Biochem. Physiol., 1982, 72B(2):195–199.

Putnam et al., The effect of variations in dietary fatty acids on the fatty acid composition of erythrocyte phosphatidylcholine and phosphatidylethanolamine in human infants, Am. J. Clin. Nutr., 1982, 36:106–104.

Yuhas et al., Human Milk Fatty Acid Composition from Nine Countries Varies Most in DHA, Lipids, Sep. 2006, 41:851–858.

Jareonkitmongkol et al., Fatty acid desaturation–defective mutants of an arachidonic–acid–producing fungus, *Mortierella alpina* 1S–4, J Gen. Micorbio., 1992, 138:997–1002.

Novel Foods Unit, Arachidonic acid rich oil SUNTGA 40S. Assessment of safety for the consumer, in accordance with European Regulation 258/97 concerning novel foods and novel food ingredients, Oct. 19, 2005, pp. 1–55, MEB, The Netherlands.

Burley et al., Egg Yolk: Structure and Properties, The Avian Egg Chemistry and Biology, 1989, Chp. 7, pp. 171–183.

Young, The Chemical & Physical Properties of Crude Fish Oils for Refiners & Hydrogenators, Fish Oil Bulletin, Jun. 1986, No. 18, pp. 1–18.

"Estimated infant formula ad expenditures in U.S." from "Breastfeeding: Some Strategies Used to Market Infant Formula May Discourage Breastfeeding; State Contracts Should Better Protect Against Misuse of WIC Name," p. 26, http://www.gao.gov/new.items/d06282.pdf (accessed Jun. 25, 2009).

Press Releases entitled "Martek Signs Multi–Year Sole–Source Supply Agreement with Hero," Martek Biosciences Corporation (2008).

Press Releases entitled "Martek Signs Multi-Year Worldwide Sole Source Supply Agreement with Abbott," Martek Biosciences Corporation (2007).

Press Releases entitled "Martek Sole-Source ARA Supply Agreement with Lactalis Nutrition Sante," Martek Biosciences Corporation (2009).

Press Releases entitled "Martek is Now the Sole-Source Supplier of ARA for all Infant Formula Products Manufactured by Hochdorf Nutricate," Martek Biosciences Corporation (2008).

Press Releases entitled "Martek Signs Multi-Year Sole-Source Supply Agreement with Numico," Martek Biosciences Corporation (2008).

Press Releases entitled "Martek to be the Sole-Source Supplier of DHA and ARA for Prodigy Brand Infant Formula Products in China," Martek Biosciences Corporation (2009).

Press Releases entitled "Martek to be the Sole-Source Supplier of DHA and ARA for Infant Formulas Produced by Grupo Ricap," Martek Biosciences Corporation (2008).

Press Releases entitled "Martek and Hain Celestial Sign Exclusive Supply Agreement for Infant Formula Products," Martek Biosciences Corporation (2006).

Birch, et al., 1998, "Visual acuity and the essentiality of docosahexaenoic acid and arachidonic acid in the diet of term infants," *Pediatr. Res.*, 44:201–209; (1998).

Carlson, et al. Inform Abstract (1990).

Clandinin, et al., "Requirements of Newborn Infants for Long Chain Polyunsaturated Fatty Acids", Acta. Paediatr. Scand. Suppl., 351:63–71.

Clandinin, et al., 2005 "Growth and development of preterm infants fed infant formulas containing docosahexaenoic acid and arachidonic acid, " *J. Pediatr.*, 146:461–468.) (1989).

Harris, et al. (*Am. J. Clin. Nutr.* 1984;40:780–85).

Innis, "Essential Fatty Acids in Growth and Development", Prog. Lipid Res., 30(1):39–103 (1991).

Jensen, Textbook Gastroenterol. Nutr. in Infancy, 1989, Chap. 17 (89b")).

O'Connor, et al., 2001, "Growth and development of preterm infants fed long-chain polyunsaturated fatty acids: a prospective, randomized controlled trial," *Pediatr.*, 108:359–371.

Beach and Holtz, BioChim. BioPhys. Acta, 316, 56–65 (1973).

Carlson et al., Am J. clin. Nutr., 44:798–804 (1986).

Robert G. Jensen, The Lipids of Human Milk (1989).

Yamada et al., Dispersion Sci. Tech., 10(4&5), 561–579 (1989).

US 5,374,657 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–8, 10–18 and 20 are cancelled.

New claims 23–34 are added and determined to be patentable.

Claims 9, 19, 21 and 22 were not reexamined.

23. *Infant formula comprising a blend of a microbial oil enriched in DHA and a microbial oil enriched in ARA, wherein the DHA and ARA are in the form of triglycerides and the oils are blended to provide a ratio of about 2 to 12 parts ARA and about 1 to 5 parts DHA, the amount of DHA-containing oil and the amount of ARA-containing oil are sufficient to provide amounts of ARA and DHA comparable to the amounts of DHA and ARA in human breast milk and the formula further comprises EPA in a maximum amount of about one twentieth the amount of ARA, wherein the only source of long chain PUFAs in said infant formula is said microbial oil enriched in DHA and said microbial oil enriched in ARA.*

24. *A process for supplementing infant formula with DHA and ARA which comprises:*
  (a) *preparing an oil blend consisting essentially of a microbial oil enriched in DHA and a microbial oil enriched in ARA, wherein the DHA and ARA are in the form of triglycerides, and wherein one of the oils is a DHA-containing microbial oil containing at least 35% DHA by weight and the oils are blended to provide a ratio of about 2 to 12 parts ARA and about 1 to 5 parts DHA and the oil blend further provides an EPA:ARA ratio of about 1 part EPA to from about 5 to about 20 parts ARA, and*
  (b) *adding said oil blend to said infant formula in sufficient amounts that the amounts of DHA, ARA and EPA in said formula are comparable to the amounts of DHA, ARA and EPA in human breast milk.*

25. *A process in accordance with claim 24, wherein said DHA-containing oil is obtained by cultivating a DHA-producing species of Crypthecodinium.*

26. *A composition consisting essentially of a blend of a microbial oil enriched in DHA and a microbial oil enriched in ARA, wherein the oils are blended to provide a ratio of about 2 to 12 parts ARA and about 1 to 5 parts DHA, wherein the DHA and ARA are in the form of triglycerides, and wherein one of the oils is a DHA-containing microbial oil containing at least 35% DHA by weight.*

27. *A composition in accordance with claim 26, wherein the oil enriched in DHA was produced by cultivating a DHA-producing species of Crypthecodinium under DHA-producing conditions.*

28. *Infant formula in accordance with claim 23, wherein the oils are further blended with vegetable oil which does not contain any long chain PUFAs.*

29. *Infant formula in accordance with claim 23 or 28, wherein the microbial oil enriched in DHA comprises at least about 25% DHA.*

30. *Infant formula in accordance with claim 29, wherein the microbial oil enriched in DHA comprises at least about 35% DHA.*

31. *Infant formula in accordance with claim 23 or 28, a composition in accordance with claim 26, or a process in accordance with claim 24, wherein the microbial oil enriched in ARA comprises at least about 20% ARA.*

32. *Infant formula in accordance with claim 23 or 28, a composition in accordance with claim 26, or a process in accordance with claim 24, wherein the oils are blended to provide a ratio of ARA:DHA of about 2:1.*

33. *Infant formula in accordance with claim 23 or 28, a composition in accordance with claim 26, or a process in accordance with claim 24, wherein the oil enriched in ARA was produced by cultivating Mortierella alpina under conditions which will induce the production of an oil enriched in ARA.*

34. *Infant formula in accordance with claim 23 or 28, wherein the oil enriched in DHA was produced by cultivating a DHA-producing species of Crypthecodinium under DHA-producing conditions.*

* * * * *